United States Patent [19]

Telschow

[11] Patent Number: 5,536,862
[45] Date of Patent: Jul. 16, 1996

[54] PENTAERYTHRITOL PHOSPHATE ALCOHOL-CONTAINING PHOSPHONATE AND PHOSPHITE COMPOUNDS

[75] Inventor: Jeffrey E. Telschow, Tarrytown, N.Y.

[73] Assignee: Akzo Nobel N.V., Arnhem, Netherlands

[21] Appl. No.: 438,151

[22] Filed: May 9, 1995

[51] Int. Cl.[6] .................................................. C07F 9/6571
[52] U.S. Cl. ........................................................... 558/74
[58] Field of Search ................................................ 558/74

[56] References Cited

U.S. PATENT DOCUMENTS

| | | | |
|---|---|---|---|
| 3,310,609 | 3/1967 | Baranauckas et al. | 260/927 |
| 3,873,496 | 3/1975 | Hills | 260/45.8 R |
| 3,883,478 | 5/1975 | Gresham | 260/45.8 |
| 3,944,633 | 3/1976 | Gresham | 260/927 R |
| 4,140,856 | 2/1979 | Bost et al. | 544/195 |
| 4,341,694 | 7/1982 | Halpern | 252/606 |
| 4,480,093 | 10/1984 | Halpern et al. | 544/195 |
| 4,584,331 | 4/1986 | Tamura et al. | 529/119 |
| 4,801,625 | 1/1989 | Parr et al. | 523/179 |
| 5,235,085 | 8/1993 | Telschow et al. | 558/74 |
| 5,362,898 | 11/1994 | Telschow | 558/74 |
| 5,420,326 | 5/1995 | Telschow | 558/74 |

FOREIGN PATENT DOCUMENTS 889338  2/1962  United Kingdom .

OTHER PUBLICATIONS

Derwent Patent Abstract No. 50190w/30 abstracting Japanese Patent Publication No. 50/046,580, published Apr. 25, 1975.

Chemical Abstracts Abstract No. 83(12):98541p abstracting Japanese Patent Publication No. 50/046,580, published Apr. 25, 1975.

R. N. Gubaidullin, Izv. Akad. Nauk SSSR, Ser. Khim. (5), 1116–1118 (1973).

*Primary Examiner*—Johann Richter
*Assistant Examiner*—Laura L. Stockton
*Attorney, Agent, or Firm*—Richard P. Fennelly; Louis A. Morris

[57] ABSTRACT

(Pentaerythritol phosphate alcohol)(aryl) phosphonate compounds may contain from one to three pentaerythritol phosphate alcohol groups, such as bis(pentaerythritol phosphate alcohol)(pentaerythritol phosphate alcohol) phosphonate, and are useful as flame retardants. The analogous phosphite compounds are also disclosed.

14 Claims, No Drawings

PENTAERYTHRITOL PHOSPHATE ALCOHOL-CONTAINING PHOSPHONATE AND PHOSPHITE COMPOUNDS

BACKGROUND OF THE INVENTION

Various derivatives of pentaerythritol phosphate are known as flame retardant additives for polymers such as polypropylene. A recent example is provided by U.S. Pat. No. 4,801,625 to W. J. Parr et al. which describes ether, ester and carbonate derivatives of pentaerythritol phosphate. The carbonate version of such compounds can be advantageously prepared by the reaction of pentaerythritol phosphate alcohol with a dihydrocarbyl carbonate as described in U.S. Pat. No. 5,235,085.

U.S. Pat. No. 3,883,478 to J. T. Gresham discloses flame retarded polyester fibers containing a flame retardant additive of phosphate compounds of the formula:

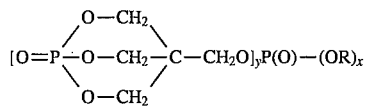

where R is an aryl radical selected from certain unsubstituted and substituted phenyl and naphthyl radicals, y is an integer of from 1 to 3, and x is 3-y.

U.S. Pat. No. 5,362,898 of J. E. Telschow describes and claims certain bis(pentaerythritol phosphate alcohol) alkylphosphonate compounds of the formula:

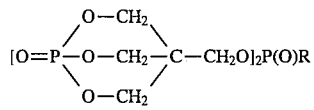

where R is alkyl, for example alkyl of from one to four carbon atoms, preferably methyl.

More recently, U.S. Pat. No. 5,420,326 of J. E. Telschow describes and claims certain bis(pentaerythritol phosphate alcohol) hydrogen phosphonate compounds of the formula given above where R is hydrogen.

SUMMARY OF THE INVENTION

One embodiment of the present invention relates to (aryl) (pentaerythritol phosphate alcohol) phosphonate compounds which may contain from one to three pentaerythritol phosphate alcohol ("PEPA") groups, such as bis(pentaerythritol phosphate alcohol) (pentaerythritol phosphate alcohol) phosphonate Another embodiment of the present invention are the corresponding (pentaerythritol phosphate)-containing phosphite compounds.

Description of the Preferred Embodiments

The (pentaerythritol phosphate alcohol)(aryl) phosphonate compounds which may contain from one to three pentaerythritol phosphate alcohol groups, such as the preferred bis(pentaerythritol phosphate alcohol)(pentaerythritol phosphate alcohol) phosphonate, have the following general formula:

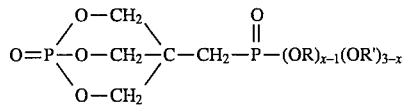

where R is derived from pentaerythritol phosphate alcohol and has the following formula

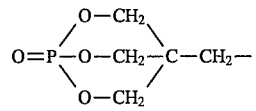

with R' being an aryl radical, such as an unsubstituted or substituted phenyl or naphthyl radical, and x is an integer of from 1 to 3. Bis(pentaerythritol phosphate alcohol) (pentaerythritol phosphate alcohol) phosphonate is a preferred species.

The corresponding phosphite compounds have the following structure:

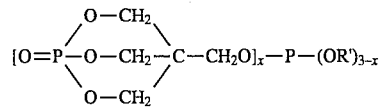

where R' and x are both as defined above. Tris(pentaerythritol phosphate alcohol) phosphite, x being equal to 3, is a preferred species.

In accordance with the present invention, the above-described phosphite compounds are first formed by the reaction of pentaerythritol phosphate alcohol with the appropriate amount of a triaryl phosphite, such as triphenyl phosphite, preferably using an appropriate transesterification catalyst, such as an alkali metal phenolate. The reaction can be conducted at elevated temperature (e.g., from about 120° C. to about 250° C.), preferably in a high boiling organic solvent, such as in an aryl phosphate solvent as described in U.S. Pat. No. 5,237,085), using one or more of such catalysts as sodium phenoxide, magnesium chloride, or the like. The phenol by-product can distill from the reaction medium during the course of the reaction.

The above-described phosphonate compounds are formed from the previously described phosphites by Arbuzov rearrangement, optionally in the presence of a rearrangement catalyst, such as iodine. Elevated temperatures of from about 180° C. to about 220° C. can be used to effectuate the desired rearrangement reaction.

The following Examples further illustrate certain embodiments of the present invention.

EXAMPLE 1

A 500 mL, four-necked, mechanically stirred, round-bottomed flask was fitted with a pot thermometer and a 3.5" Vigreux column topped with a distillation head and receiver. The flask was charged with 72.0 grams (0.40 moles) of pentaerythritol phosphate alcohol (PEPA or 2,6,7-trioxa-1-phosphabicyclo[2.2.2]octane-4 -methanol-1-oxide), 41.3 grams (0.133 mole) of triphenyl phosphite, 31 mg of sodium metal, 122 mg of phenol (to form sodium phenoxide in situ as a catalyst), and 200 mL of Phosflex® 41P from Akzo Nobel Chemicals Inc. An oil bath heated the reaction mixture to 200° C. under a vacuum of 60 nun pressure. A total of 28.4 grams (76% of theory) of phenol distilled from the reaction vessel. Analysis by $^{31}P$ NMR ($d_6$-DMSO) of the white solid which formed showed resonances at +137.1 and −6.2 ppm in a ratio of 1:3 for tris-PEPA phosphite (phosphorous acid, tris(2,6,7-trioxa-1-phosphabicyclo[2.2.2]oct-4ylmethyl) ester, P, P', P"-trioxide) and resonances for a phosphonate rearrangement product. The ratio of phosphite to phosphonate was 4.6:1.

EXAMPLE 2

Without isolating the product of Example 1, 127 mg (1.3 mmoles) of iodine was added to the reaction product from Example 1 and the flask was reheated to 200° C. for eight hours to continue the Arbuzov rearrangement. After cooling the reaction mixture, the white solid that was produced was filtered, was washed three times with methylene chloride, and was dried at 120°/2mm for three hours to give 70.0 grams (0.123 mole, 92.4% yield) of bis-PEPA PEPA-phosphonate (BPPP or 2,6,7-trioxa-1-phosphabicyclo[2.2.2]octane-4 -methylphosphonic acid, 1-oxide, bis(2,6,7-trioxa-1 -phosphabicyclo[2.2.2]oct-4ylmethyl) ester, P,P'-dioxide). Analysis by $^{31}$P NMR showed resonances at +28.8, −6.3, and −7.1 ppm in ratios of 1:2:1. The ratio of phosphite to phosphonate was now 1:2.8.

EXAMPLE 3

A 5 L, 4-necked, mechanically stirred, round-bottomed flask was fitted with a pot thermometer and a distillation head and receiver. The flask was then charged with 920.3 grams (5.11 moles) of PEPA, 527.5 grams (1.70 moles) of triphenyl phosphite, 1.175 grams (51 mmoles) of sodium metal, and 2556 mL of Phosflex® 41P isopropylated triphenyl phosphate. The reaction mixture was heated with a heating mantle at 30–60 mm pressure. At a pot temperature of 175° C., rapid phenol distillation began. The temperature rose to 218° C. over three and one half hours, at which point distillation ceased, and the receiver held 479.9 grams (97.2% of theory) of phenol. After the reaction mixture had cooled to room temperature, 649 mg (5.1mmoles) of iodine was added, and the flask was reheated under nitrogen to 220°–225° C. for six hours. The flask was then cooled, the solid product was filtered in two portions, and each portion was washed with about 400 mL of acetone. Analysis by NMR revealed the presence of residual Phosflex® 41P phosphate, but three additional 1 L acetone washings removed most of this contaminant. After drying, the off-white powdery BPPP weighed 844.9 grams (1.49 moles, 87.5% yield), showed no residual phosphite, and contained 4.1 mole % Phosflex® 41P phosphate by $^{31}$P NMR.

EXAMPLE 4

This Example shows the ability to recycle solvent and catalysts in accordance with an embodiment of the present invention.

Example 3 was repeated using the recovered Phosflex® 41P phosphate plus 250 mL of fresh solvent and no additional sodium or iodine. After the Arbuzov rearrangement step (nine hours at 225° C.) 949.7 grams (1.67 moles, 98.3 % yield) of light brown BPPP product was recovered.

EXAMPLE 5

This Example illustrates the flame retardancy characteristics of the compound of Examples 2–4 (abbreviated BPPP). This compound had a DSC exotherm onset temperature of 311° C. and a phosphorus content of 19.6%. The Table set forth below shows two samples that were tested:

| Material | Amount (Weight Percent) | |
|---|---|---|
| | Test Sample 1 | Test Sample 2 |
| Polypropylene | 69.8 | 67.5 |
| BPPP | 12.2 | 13.5 |
| Melamine Phosphate | 18.0 | 18.0 |

The Limiting Oxygen Index (LOI) data, flame retardancy test results (UL-94, 1/16 inch), and average flame time (AFT) given in seconds that were obtained are given below:

| Data/Test Result | Test Sample 1 | Test Sample 2 |
|---|---|---|
| LOI (O$_2$ %) | 29.8 | 30.0 |
| UL-94 Result | V2 | V2 |
| AFT | 8.1 | 11.1 |

The forgoing Examples illustrate certain embodiments of the invention and for that reason should not be construed in a limiting sense. The scope of protection sought is set forth in the claims which follow.

I claim:

1. (Aryl) (pentaerythritol phosphate alcohol) phosphonate of the formula:

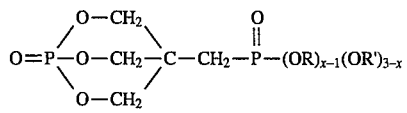

where R is derived from pentaerythritol phosphate alcohol and has the following formula

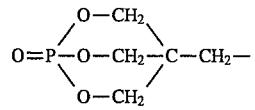

with R' being selected from the group consisting of unsubstituted phenyl, substituted phenyl, and naphthyl, and x being an integer of from 1 to 3.

2. A compound as claimed in claim 1 wherein the phosphonate contains one pentaerythritol phosphate alcohol group.

3. A compound as claimed in claim 1 wherein the phosphonate contains two pentaerythritol phosphate alcohol groups.

4. Bis(pentaerythritol phosphate alcohol) (pentaerythritol phosphate alcohol) phosphonate.

5. A compound as claimed in claim 1 wherein the aryl is phenyl.

6. A compound as claimed in claim 2 wherein the aryl is phenyl.

7. A compound as claimed in claim 3 wherein the aryl is phenyl.

8. (Pentaerythritol phosphate alcohol)(aryl) phosphite of the formula:

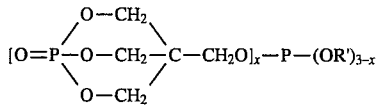

with R' being selected from the group consisting of unsubstituted phenyl, substituted phenyl, and naphthyl, and x being an integer of from 1 to 3.

9. A compound as claimed in claim 8 wherein the phosphite contains one pentaerythritol phosphate alcohol group.

10. A compound as claimed in claim 8 wherein the phosphite contains two pentaerythritol phosphate alcohol groups.

11. Tris(pentaerythritol phosphate alcohol) phosphite.

12. A compound as claimed in claim 8 wherein the aryl is phenyl.

13. A compound as claimed in claim 9 wherein the aryl is phenyl.

14. A compound as claimed in claim 10 wherein the aryl is phenyl.

* * * * *